United States Statutory Invention Registration [19]

[11] Reg. Number: H890

Rorer [43] Published: Feb. 5, 1991

[54] HERBICIDAL HETEROCYCLICBENZYLSULFONAMIDES

[76] Inventor: Morris P. Rorer, 64 Lower Valley La., Green Valley, Newark, Del. 19711

[21] Appl. No.: 312,654

[22] Filed: Feb. 21, 1989

Related U.S. Application Data

[60] Division of Ser. No. 69,236, Jul. 2, 1987, abandoned, which is a continuation-in-part of Ser. No. 618,731, Jun. 8, 1984, abandoned.

[51] Int. Cl.[5] ..... C07C 303/00; C07C 315/00; C07C 321/00

[52] U.S. Cl. ..... 560/12; 560/9; 560/11; 562/430

[58] Field of Search ..... 560/12; 562/430

[56] References Cited

U.S. PATENT DOCUMENTS 4,420,325 9/1983 Sauers ..... 560/12

*Primary Examiner*—John S. Maples
*Assistant Examiner*—Philip Tucker

[57] ABSTRACT

Novel benzylsulfonamide compounds containing ortho-heterocyclic substitutents such as N-[(4,6-dimethoxypyrimidin-2-yl)aminocarbonyl]-2-[5-(methylthio-1,3,4-oxadiazol-2-yl]benzenemethanesulfonamide are useful as preemergent and/or postemergent herbicides or plant growth regulants.

1 Claim, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HERBICIDAL HETEROCYCLICBENZYLSULFONAMIDES

RELATED APPLICATIONS

This is a division of application Ser. No. 07/069,236, filed July 2, 1987, now abandoned, which is a continuation-in-part of my copending application U.S. Ser. No. 618,731 filed June 8, 1984, now abandoned.

BACKGROUND OF THE INVENTION

U.S. Pat. No. 4,420,325, issued Dec. 13, 1983, discloses herbicidal benzylsulfonamides of formula

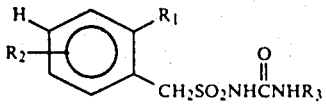

where $R_1$ is F, Cl, Br, $CF_3$, $C_1$-$C_3$ alkoxy, $C_1$-$C_3$ alkyl, $NO_2$, $CO_2R_4$, $SO_2R_5$, $SO_2NR_6R_7$, $SO_2N(OCH_3)CH_3$, $SO_2OCH_2CF_3$, $OSO_2R_5$ or $CH_2L$.

European Patent Applications (EP-A) 83,975, published July 20, 1983 and 85,476, published Aug. 10, 1983, disclose herbicidal compounds of formula

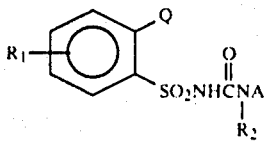

where Q is various 5- and 6-membered unsaturated, saturated and partially saturated heterocycles.

U.S. Pat. No. 4,370,480, issued Jan. 25, 1983, discloses herbicidal sulfonamides of formula

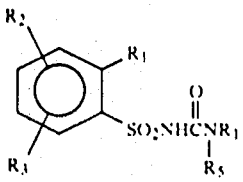

IV where $R_1$ may be

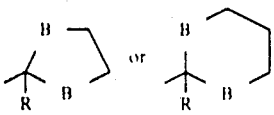

and B is O or $S(O)_G$.

SUMMARY OF THE INVENTION

This invention relates to novel compounds of Formula I, suitable agricultural compositions containing them and their method-of-use as general and/or selective preemergence and/or postemergence herbicides and/or plant growth regulants.

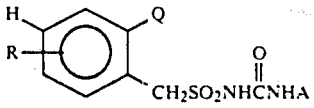

I wherein

R is H, F, Cl, Br, $CH_3$, $CF_3$, $OCH_3$, $OCHF_2$ $SCH_3$ or $SCHF_2$;

Q is a saturated, 5- or 6-membered ring containing 1 to 2 heteroatoms selected from 0-2 S or 0-2 O or an unsaturated 5- or 6-membered ring containing 1 to 3 heteroatoms selected from 0-1 S, 0-1 O or 0-3 N and Q may optionally be substituted by one or more groups selected from $C_1$-$C_4$ alkyl, halogen, $C_1$-$C_3$ alkoxy, mercapto, $C_1$-$C_3$ alkylthio, $C_1$-$C_2$ haloalkoxy, $C_3$-$C_4$ alkenylthio, $C_1$-$C_2$ haloalkylthio or $SCH_2CN$;

A is

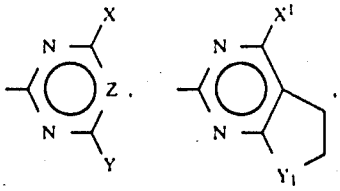

A-1 A-2

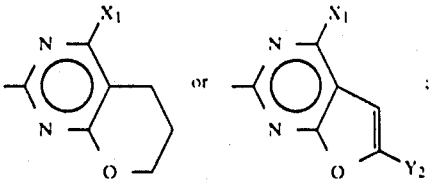

A-3 A-4

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$ or $CF_3$;

Y is H, $CH_3$, $OCH_3$, $OC_2H_5$, $CH_2OCH_3$, $NHCH_3$, $N(OCH_3)CH_3$, $C_2H_5$, $N(CH_3)_2$, $CF_3$, $SCH_3$, $OCH_2CH{=}CH_2$, $OCH_2C{\equiv}CH$, $CH_2OC_2H_5$, $OCH_2CH_2OCH_3$, $CH_2SCH_3$,

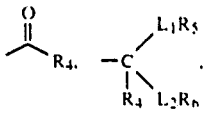

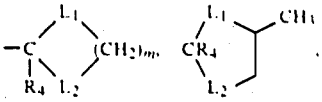

$OCF_2H$, $SCF_2H$ or cyclopropyl;

m is 2 or 3;

$L_1$ and $L_2$ are independently O or S;

$R_4$ is H or $CH_3$;

$R_5$ and $R_6$ are independently $C_1$-$C_2$ alkyl;

Z is CH or N;

$Y_1$ is O or $CH_2$;

$X_1$ is $CH_3$, $OCH_3$, $OC_2H_5$ or $OCF_2H$; and $Y_2$ is H or $CH_3$; provided that (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(b) when Q is a saturated ring containing 2 heteroatoms or an unsaturated ring containing oxygen and sulfur, said heteroatoms are not bonded directly to one another;

(c) when Q is Q-7 and $R_1$ is $SR_3$, then X is $CH_3$ or $OCH_3$, Y is $OCH_3$ and Z is CH or N; and (d) when X or Y is $OCF_2H$, then Z is CH;

and their agriculturally suitable salts.

Preferred for reasons of greater ease of synthesis and/or greater herbicidal efficacy are:

(1) Compounds of Formula I where R is H, Q is

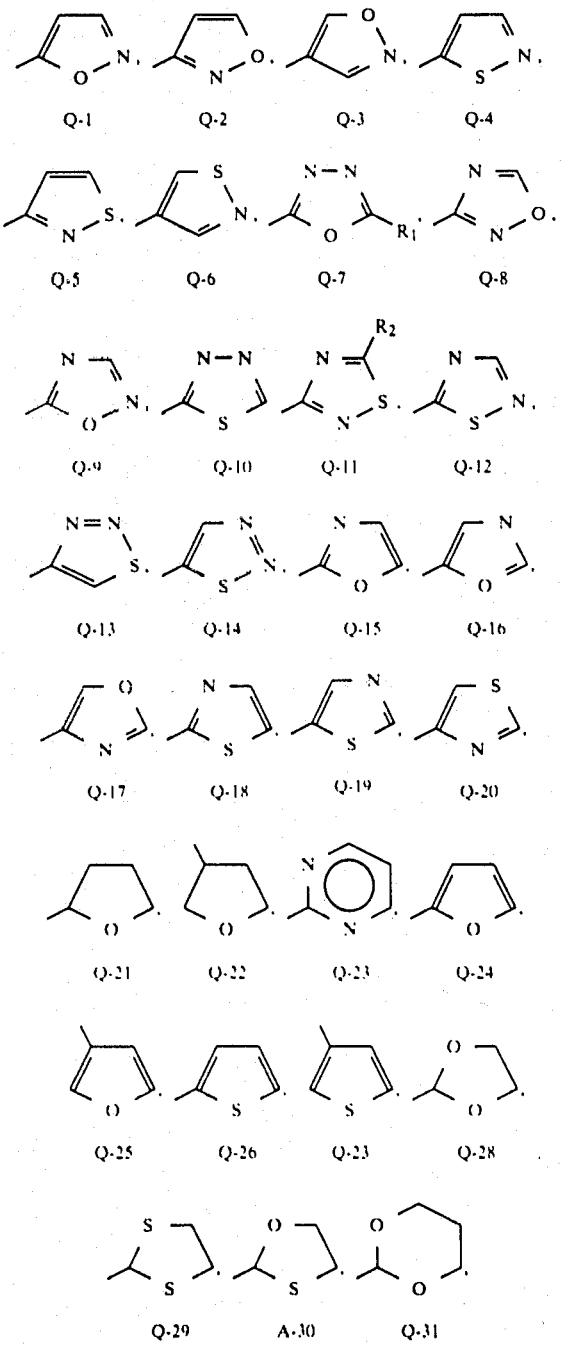

-continued

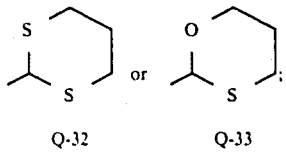

$R_1$ is H, $C_3$, $C_2H_5$, $SR_3$, $OCH_3$ or $OCH_2CH_3$;

$R_2$ is H or Cl; and $R_3$ is H, $C_1$-$C_4$ alkyl, $CH_2CN$, $CHF_2$ or $CH_2CH{=}CH_2$;

(2) Compounds of Preferred 1 where A is A-1 and Y is $CH_3$, $OCH_3$, $CH_2OCH_3$, $NHCH_3$, $CH_2CH_3$, $CH(OCH_3)_2$ or cyclopropyl;

(3) Compounds of Preferred 2 where X is $CH_3$, $OCH_3$, Cl, Br or $OCF_2H$;

(4) Compounds of Preferred 3 where Q is Q-1, Q-2 or Q-3;

(5) Compounds of Preferred 3 where Q is Q-4, Q-5 or Q-6;

(6) Compounds of Preferred 3 where Q is Q-7, Q-8 or Q-9;

(7) Compounds of Preferred 6 where Q is Q-7;

(8) Compounds of Preferred 3 where Q is Q-10; Q-11, Q-12, Q-13 or Q-14;

(9) Compounds of Preferred 3 where Q is Q-15; Q-16 or Q-17;

(10) Compounds of Preferred 3 where Q is Q-18, Q-19 or Q-20;

(11) Compounds of Preferred 3 where Q is Q-21 or Q-22;

(12) Compounds of Preferred 3 where Q is Q-23;

(13) Compounds of Preferred 3 where Q is Q-24, Q-25, Q-26 or Q-27;

(14) Compounds of Preferred 3 where Q is Q-28, Q-29, Q-30, Q-31, Q-32 or Q-33.

An exemplary compound of the present invention is N-[(4,6-dimethoxypyrimidin-2-yl)aminocarbonyl]-2-[5-(methylthio-1,3,4-oxadiazol-2yl]benzenemethanesulfonamide, m.p. 174°-177° C.

DETAILED DESCRIPTION OF THE INVENTION

Synthesis

The compounds of Formula I can be prepared by one or more of the methods described below in Equations 1, 2 or 3.

As shown in Equation 1 below, the compounds of Formula I can be prepared by treating sulfonamides of Formula II with the methyl ester of a pyrimidine or triazinecarbamic acid of Formula III in the presence of an equimolar quantity of trimethylaluminum.

Equation 1

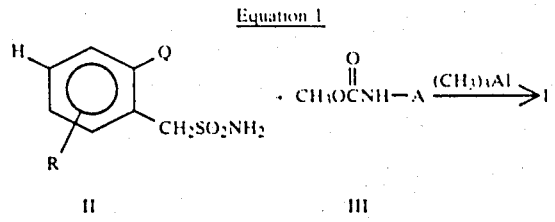

wherein Q, R and A are as previously defined.

The reaction of Equation 1 is best carried out at temperatures between 23° to 83° C. in an inert solvent such as methylene chloride or 1,2-dichloroethane for 12 to 96 hours under an inert atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride or ether or by chromatography procedures. The methyl carbamates, III, can be conveniently prepared by treatment of the corresponding heterocyclic amines of Formula VI with dimethyl carbonate or methyl chloroformate in the presence of a base such as sodium hydride or pyridine.

Further details of this reaction and the preparation of the carbamates of Formula III can be found in EP-A No. 83,975 (published July 20, 1983).

Alteratively, compounds of Formula I can be prepared by the reaction of sulfonamides of Formula II with the phenyl ester of the appropriate carbamic acid, IV, in the presence of an equimolar quantity of a tertiary amine base such as 1,8-diazabicyclo[5.4.0]-undec-7-ene (DBU).

Equation 2

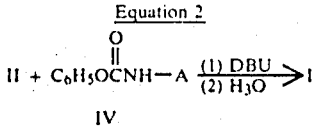

wherein A is as previously defined.

The reaction of Equation 2 is best carried out at 20° to 30° C. in an inert solvent such as dioxane or acetonitrile. Aqueous acid work-up affords the desired products, according to the teachings of EP-A No. 70,804 (published Jan. 26, 1983) and South African Patent Application Nos. 825,042 and 830,441. The phenyl carbamates, IV, can be synthesized by treating the corresponding heterocyclic amines of Formula VI with diphenyl carbonate or phenyl chloroformate in the presence of a base such as sodium hydride or pyridine.

Also, many components of Formula I can be prepared by reacting an appropriate sulfonyl isocyanate, V, with the appropriately substituted aminoheterocycle, VI, as shown in Equation 3 below.

Equation 3

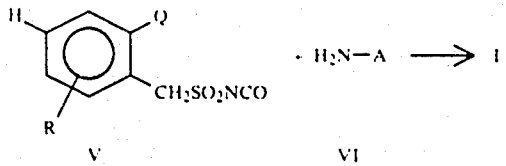

wherein R and A are as previously defined; and Q is Q-1 to Q-22 and Q-24 to Q-27.

The reaction is best performed in an inert solvent such as methylene chloride, tetrahydrofuran, acetonitrile or toluene at 23° to 100° C. for 1 to 24 hours. In cases where the products are insoluble in the reaction solvent, they may be isolated by simple filtration. When the products are soluble, they may be isolated by evaporation of the solvent and trituration of the residue with an appropriate solvent such as 1-chlorobutane, diethyl ester, methanol or ethyl acetate and filtration.

Sulfonyl isocyanates of Formula V above may be prepared, although often times in low yields, from corresponding sulfonamides of Formula II by methods analogous to those described in U.S. Pat. Nos. 4,238,621, 4,420,325 (issued Dec. 13, 1983) and EP-A No. 83,975 (published July 20, 1983). By a preferred method, sulfonamides are reacted with phosgene, in the presence of n-butyl isocyanate and a tertiary amine catalyst, at reflux in an inert solvent such as xylenes. A preferred catalyst is 1,4-diazabicyclooctane-[2.2.2]octane (DABCO). Alternatively, isocyanates, V, may be prepared by (1) reacting sulfonamides, II, with n-butyl isocyanate and a base such as potassium carbonate at reflux in an inert solvent such as 2-butanone to form a n-butyl sulfonylurea; and (2) reacting this compound with phosgene and DABCO catalyst at reflux in xylenes solvent.

Benzenemethanesulfonamides of Formula II can be prepared from appropriately substituted benzyl chlorides or benzyl bromides of Formula VII by a sequence of reactions described in Equation 4 below.

Equation 4

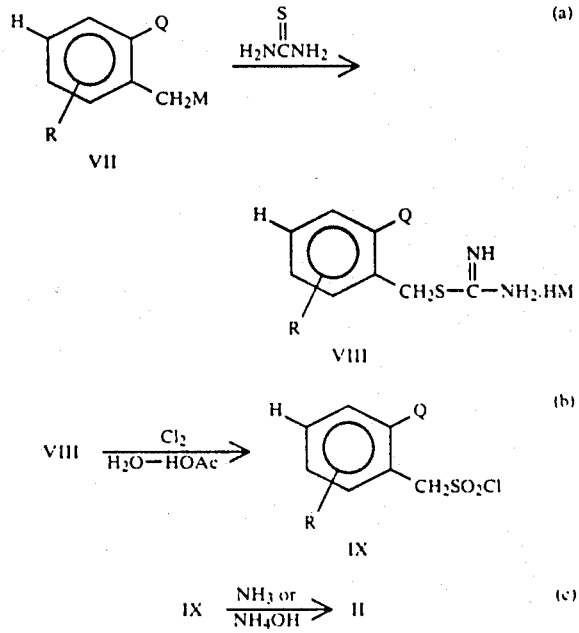

wherein M is chlorine or bromine; R is as originally defined; except R is not $SCH_3$ or $SCF_2H$; Q is Q-1 to Q-20, and Q-23.

Reaction 4(a)

The conversion of alkyl halides to isothiouronium salts is well precedented in the literature. For relevant examples, see T. B. Johnson and J. M. Sprague, *J. Am. Chem. Soc.*, 58, 1348 (1936); 59, 1837 and 2439 (1937); 61, 176 (1939). In a typical procedure, a benzyl halide of Formula VII is treated with thiourea in a suitable solvent such as ethanol or tetrahydrofuran. Temperatures of 40°-80° C. over one-half to 4 hours are typically required to complete the reaction. The product salts, VIII, are isolated by cooling and filtration or by concentration to remove the solvent. The salts, VIII, are generally sufficiently pure to be carried on directly to step 4(b) without further purification.

Reaction 4(b)

The oxidative chlorination of isothiouronium salts to afford sulfonyl chlorides is most conveniently effected according to the procedure of Johnson as described in *J. Am. Chem. Soc.*, 61, 2548 (1939). Thus, the appropriate isothiouronium salts, VIII, are suspended in aqueous acetic acid and treated with at least three equivalents of chlorine at temperatures between 0° and 20° C. The product sulfonyl chlorides of Formula IX are isolated by filtration or extraction into methylene chloride followed by drying and evaporation of the solvent. No further purification of the sulfonyl chlorides is generally necessary.

Reaction 4(c)

The conversion of sulfonyl chlorides to sulfonamides is well precedented in the literature. For example, exposure of a sulfonyl chloride to ammonium hydroxide results in the formation of the corresponding sulfonamide, e.g., Crossley et al., *J. Am. Chem. Soc.*, 60, 2223 (1938). Also, sulfonyl chlorides IX can be suspended in an aprotic solvent such as diethyl ether, 1-chlorobutane, methylene chloride, or tetrahydrofuran and contacted with an excess of anhydrous ammonia at a temperature of about −20° to 25° C. The product sulfonamides, II, are isolated by filtration and washing with water to remove the by-product ammonium chloride, and concentrating the organic solution. The crude sulfonamides, II, can be purified by recrystallization or chromatography procedures.

Alternatively, sulfonamides of Formula II may be prepared from the appropriate benzyl halides of Formula VII by a three-step sequence of reactions shown below in Equation 5.

Equation 5

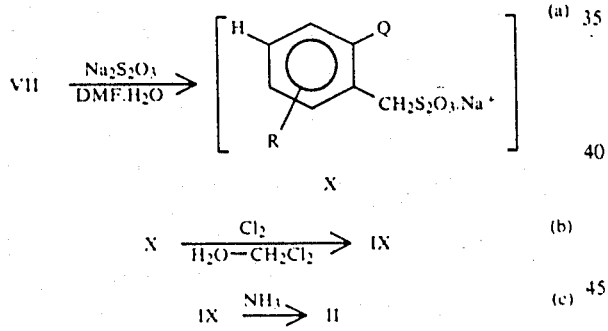

wherein R and Q are as previously defined.

Reaction 5(a)

The displacement reactions are best carried out by treating the benzyl halides, VII, with excess sodium thiosulfate (generally about 10 to 30% mole excess) at about 40° to 90° C. for one to 24 hours in an aqueous N,N-dimethylformamide (DMF) solvent. Preferably, sufficient water is used to insure solubility of the sodium thiosulfate. After the reaction is complete, the suspension is cooled and added to excess water. After washing the aqueous suspension with methylene chloride to remove insoluble impurities, the aqueous solution, containing thiosulfate salt, X, is reacted directly as shown in Equation 5(b) without isolation of X.

Reaction 5(b)

The oxidative chlorination of thiosulfate salt, X, is most conveniently effected by addition of methylene chloride solvent to the aqueous solution of Equation 5(a) and treating the suspension with excess chlorine (at least three equivalents, preferably three to five equivalents) at temperatures between 0° to 20° C. The reaction generally requires about 0.5 to 5 hours at 0° to 20° C. After completion of reaction, crude sulfonyl chlorides, IX, are isolated by separation, drying and evaporation of the methylene chloride layers.

Reaction 5(c)

The amination reaction of Equation 5(c) is carried out as described above for Equation 4(c).

Also, certain sulfonamides of Formula II may be prepared from appropriately substituted o-(methoxycarbonyl)benzenemethanesulfonamides, VII, as shown in Equation 6 below.

Equation 6

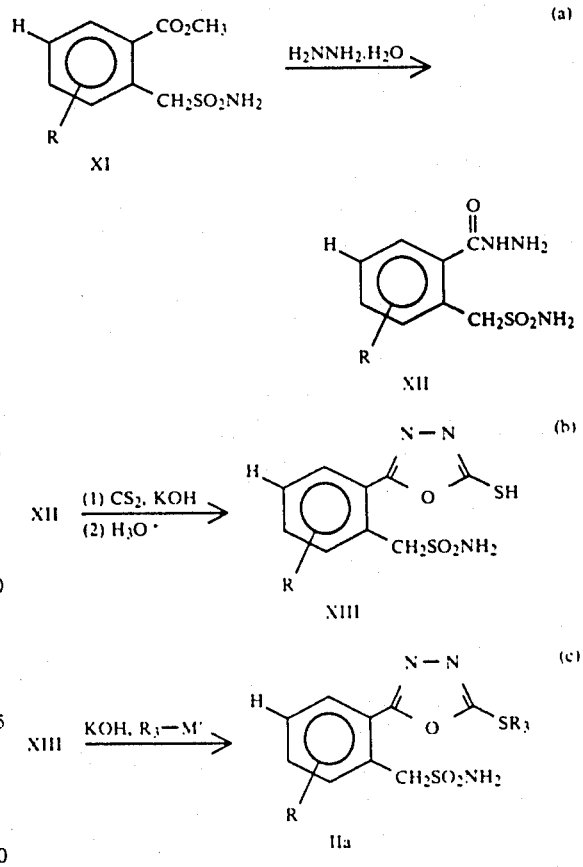

wherein M' is Cl, Br or I; and R and $R_3$ are as previously defined.

Reaction 6(a)

The conversion of carboxylic esters to hydrazides is well known in the literature. In a typical procedure, a carboxylic ester of Formula XI is reacted with an excess of hydrazine monohydrate (about 10 to 30% mole excess) in an inert solvent such as methanol or ethanol at reflux for one to 24 hours. The hydrazide products, XII, are isolated by cooling and filtration or by concentration to remove the solvent and triturating the hydrazide residue, XII, with water. The hydrazides, XII, are generally sufficiently pure to be carried on directly to step 6(b), but may be purified further by recrystallization procedures. Esters of the general Formula XI are known; see U.S. Pat. No. 4,420,325.

Reaction 6(b)

The conversion of hydrazides to 2-mercaptooxidiazoles is also well known in the literature, e.g., R. W. Young and K. H. Wood, *J. Am. Chem. Soc.*, 77, 400 (1955). In a typical procedure, hydrazides, XII, are heated under reflux with equimolar amounts of potassium hydroxide and an excess of carbon disulfide in methanol or ethanol solvent until the evolution of hydrogen sulfide has nearly stopped. Oxadiazoles, XIII, are isolated by concentration of the solvent, addition of water to the residue, filtration of the aqueous suspension to remove insoluble impurities, acidification with hydrochloric acid of the aqueous filtrate and filtration. Oxadiazoles, XIII, are generally pure enough to carry on to step 6(c), but may be further purified by recrystallization procedures.

Reaction 6(c)

Alkylation of 2-mercaptooxidazoles is also well known in the literature, e.g. S. Girl et al., *Agr. Biol. Chem.*, 40, 17 (1976). Typically, oxidazoles, XIII, are reacted with an equimolar amount of a base such as potassium hydroxide and excess alkylating agent, $R_3$—M', at reflux temperatures in an inert solvent such as methanol or ethanol for 0.5 to 24 hours. Sulfonamides, IIa, are isolated by concentration of the solvent, addition of water to the residue and filtration. For the case where $R_3$=$CF_2H$, the reaction is preferably run in DMF solvent at 60°-90° C. with excess potassium carbonate as base. Products IIa, isolated by addition of water and filtration, may be further purified by recrystallization procedures.

Benzyl halides of Formula VII, where Q is Q-1 to Q-20 and Q-23, may be prepared as shown below in Equation 7 by treatment of the appropriately substituted toluene derivatives, XIV, with either N-bromosuccinimide (NBS) or N-chlorosuccinimide (NCS).

Equation 7

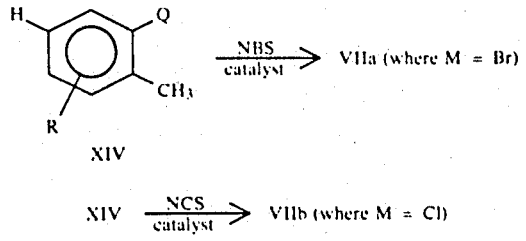

where R is as previously defined; and Q is Q-1 to Q-20 and Q-23.

The reactions of Equation 7 can be most conveniently carried out by heating a solution of the toluene derivatives, XIV, and either N-bromosuccinimide or N-chlorosuccinimide in a suitable solvent such as carbon tetrachloride at reflux temperature. A free radical catalyst such as azoisobutyronitrile or benzoyl peroxide is usually employed to initiate the reaction. When the reaction is complete, the cooled solution is filtered to remove the by-product succinimide and the filtrate concentrated in vacuo. The benzyl halides of Formula VIIa and VIIb are often obtained in a sufficiently pure state for further transformation. They may, however, be further purified by recrystallization or chromatography procedures obvious to those skilled in the art.

Benzyl halides of Formula VII containing an o-furan or thiophene group (Q is Q-24 to Q-27) may be prepared by the sequence of reactions shown below in Equation 8.

Equation 8

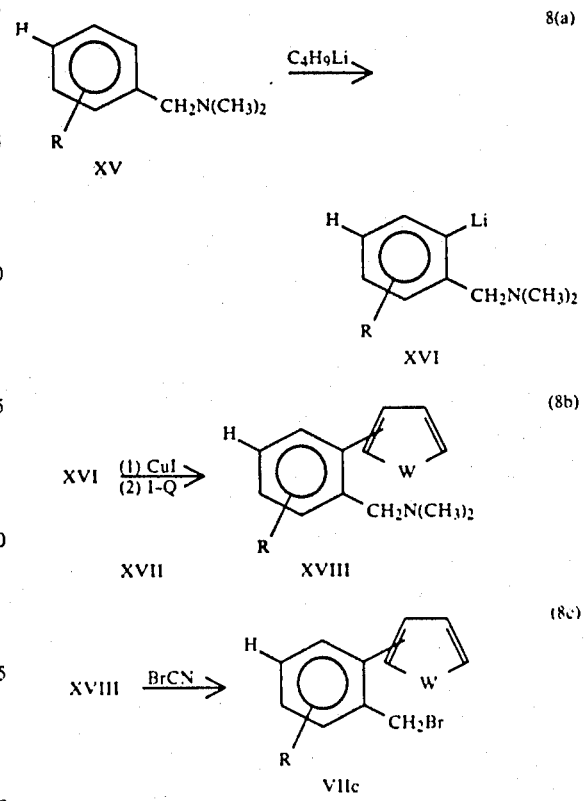

wherein R is H; W is O or S; and Q is Q-24 to Q-27.

Equation (8a,b)

A N,N-dimethylbenzylamine of Formula XV is dissolved in an ethanol solvent, such as tetrahydrofuran, and one equivalent or n-butyllithium in hexane is added at 0°-25° C. After 1-5 hours at 0°-25°, the compound of Formula XVI is formed. This is not isolated, but one equivalent of a copper(I) iodide salt is added at −20° to 0°, followed by 1-1.5 equivalents of an appropriate iodofuran or iodothiophene of Formula XVII. The reaction mixture is then heated at 40°-70° C. for 1-3 days, concentrated, poured onto aqueous ammonia, extracted with methylene chloride, dried and concentrated to provide compounds of Formula XVIII. The compounds are further purified by chromatography procedures obvious to one skilled in the art.

Equation 8(c)

The compounds of Formula XVIII are treated with cyanogen bromide in an ethereal solvent, such as tetrahydrofuran, and stirred at 20°-70° C. for one to 24 hours to provide benzyl bromides of Formula VIIc, according to teachings of *Org. React.*, 7, 198 (1953) and *Ber.*, 43, 3209 (1910). The compounds are isolated by concentration in vacuo and purified by chromatography procedures.

Alternatively, benzyl halides of Formula VIIc above may be prepared by the sequence of reactions shown below in Equation 9.

Equation 9

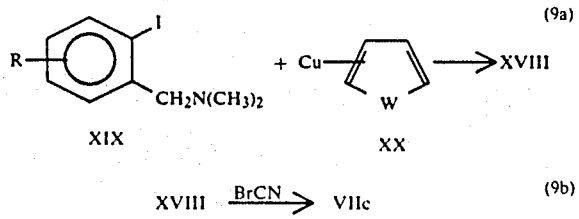

wherein R is as originally defined; and W is O or S.

Reaction 9(a)

In this reaction a furyl- or thienylcopper compound of Formula XX is reacted with an appropriate N,N-dimethyl-o-iodobenzylamine of Formula XIX in a solvent such as pyridine or quinoline. The copper compounds of Formula XX are prepared by reacting the corresponding lithium compounds with cuprous iodide or cuprous bromide in a solvent such as diethyl ether. The detailed procedures for analogous types of reactions are described in the following references: M. Nilsson and C. Ullenius, *Acta. Chem. Scand.*, 24, 2379-2388 (1970); C. Ullenius, *Acta. Chem. Scand.*, 26, 3383-3386 (1972).

Reaction 9(b)

This reaction is run similar to that described in Equation 8(c).

Benzyl halides of Formula VII containing a tetrahydrofuran group (Q is Q-21 or Q-22) may be prepared by the sequence of reactions shown below in Equation 10.

Equation 10

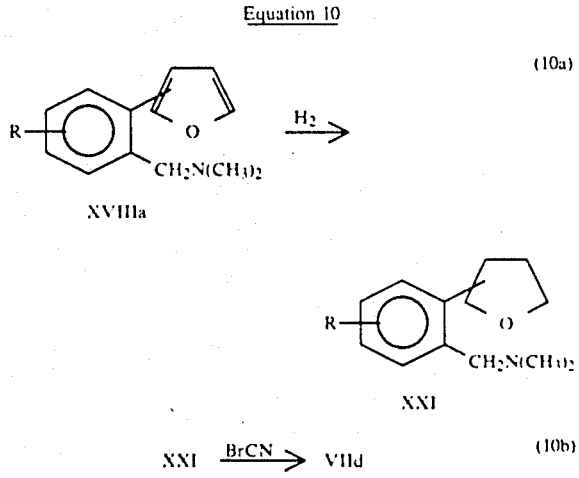

wherein R is as originally defined.

Reaction 10(a)

Reductions of furans to tetrahydrofurans are will known in the literature. The choice of catalyst, solvent, pressure and temperature for such reductions has been reviewed by Samuel Sevadash in *The Furans* by A. P. Dunlop and F. N. Peters, Reinhold Publishing Corporation, New York, N.Y., 1953, pp. 674-713; and by P. N. Rylander in *Catalytic Hydrogenation in Organic Synthesis*, Academic Press, 1979, pp. 227-234.

The o-heterocyclic toluenes of Formula XIV above are important intermediates for the preparation of many of the compounds of this invention. They can be prepared by those skilled in the art by the application of appropriate methods selected from the variety of known literature procedures for preparing substituted aromatic heterocycles.

For instance, as illustrated in equation 11(a) below, EP-A No. 83,975 (published July 20, 1983), and references cited therein, teach methods for transforming various o-(substituted)nitrobenzenes of Formula XXII to o-(heterocyclic)nitrobenzenes of Formula XXIII, where Q is Q-1 to Q-20. As illustrated in Equation 11(b) below, by substituting similarly substituted o-(substituted)toluenes of Formula XXIV for nitrobenzenes, XXII, and carrying out the appropriate reactions taught in EP-A No. 83,975, or simple modifications thereof, those skilled in the art can prepare compounds of Formula XIVa, where Q is Q-1 to Q-20.

Equation 11

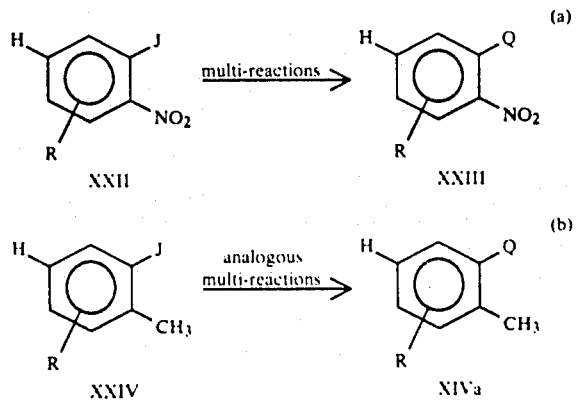

wherein R is as originally defined; Q is Q-1 to Q-20; and J is an appropriate functional group taught in EP-A No. 83,975, and references cited therein, to prepare ortho-groups Q-1 to Q-20.

In addition, o-(pyrimidin-2-yl)toluenes of Formula XIVb, where Q is Q-23, are prepared from amidine salts, XXV, as shown in Equation 12.

Equation 12

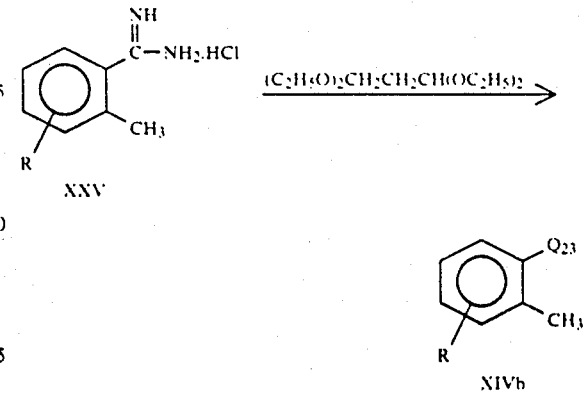

wherein R and Q-23 are as previously defined.

The reaction of Equation 12 is accomplished by heating salts, XXV, with 1,1,3,3-tetraethoxy (or methoxy)-propane in an inert solvent such ethanol at 25°-80° C. for about 1 to 10 hours. The products, XIVb, are isolated by addition of water, extraction with methylene chloride, drying and concentration of the filtrate.

The sulfonamides of Formula II, substituted by an o-cyclic-acetal or thioacetal group (Q is Q-28 to Q-33), may be prepared by known methods obvious to those skilled in the art.

The heterocyclic amine intermediates such as those depicted by Formula VI above in Equation 3 can be prepared by methods known in the literature, or simple modifications thereof, by those skilled in the art. For instance, the synthesis of aminopyrimidines and triazines has been reviewed in "The Chemistry of Heterocyclic Compounds", a series published by Interscience Publishers, Inc., New York and London. Aminopyrimidines are also described by D. J. Brown in the "Pyrimidines", Vol. 16 of this series. Aminotriazines are also reviewed by E. M. Smolin and L. Rapaport in "s-Triazines and Derivatives", Vol. 13 of the same series. The synthesis of triazines is also described by F. C. Schaefer U.S. Pat. No. 3,154,547 and by K. R. Huffman and F. C. Schaefer, *J. Org. Chem.*, 28, 1812 (1963).

The 5,6-dihydrofuropyrimidin-2-amines, the cyclopentapyrimidin-2-amines (VI, A is A-2) and the 6,7-dihydro-5H-pyranopyrimidin-2-amines (VI, A is A-3) are prepared as described in EP-A No. 15,683. Synthesis of the furopyrimidin-2-amines (VI. A is A-4) are described in EP-A No. 46,677, Pyrimidine and triazine amines in which Y is such groups as dialkoxymethyl of 1,3-dioxolan-2-yl are prepared as described in EP-A No. 84,224 (published July 27, 1983). Also, South African Patent Application No. 837,434 (published Oct. 5, 1983) describes methods for the synthesis of cyclopropylpyrimidines and triazine amines substituted by such groups as halogen, alkyl, haloalkyl, alkoxy, haloalkoxy, amino, alkylamino, dialkylamino or alkoxyalkyl. Also, South African Patent Application Nos. 825,045, and 825,671 describe methods for the synthesis of aminopyrimidines and triazines substituted by such groups as haloalkoxy or haloalkylthio, e.g., $OCH_2CH_2Cl$, $OCH_2CF_3$ or $SCF_2H$.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another.

Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compound of this invention is further illustrated by the following specific examples. Unless otherwise indicated, temperatures are in degrees centigrade.

EXAMPLE 1

2-[(Aminosulfonyl)methyl]benzoic acid hydrazide

To a suspension of 84 g of methyl 2-[(aminosulfonyl)-methyl]benzoate in 300 ml of absolute ethanol was added dropwise 22 g of hydrazine monohydrate. The thick suspension was heated at reflux for about 16 hours to yield a solution, then a thick suspension, at reflux temperature. The suspension was cooled to 20° C., filtered, and the residue was washed 1×100 ml of water and suction dried about three hours to provide 49 g of the subject compound; m.p. 221°-222° C.

Anal. calc. for $C_8H_{11}N_3O_3S$: C,41.9; H,4.8; N,18.3; Found: C,42.5; H,4.8; N,18.5.

EXAMPLE 2

2-(5-Mercapto-1,3,4-oxidazol-2-yl)benzenemethanesulfonamide

To a suspension of 11.5 g of the hydrazide prepared in Example 1 in 100 ml of absolute ethanol was added a solution of 2.8 g of potassium hydroxide in 20 ml of water. After stirring several minutes, 4.8 g of carbon disulfide was added in one portion. The suspension was refluxed 4.5 hours then concentrated in vacuo. After water (about 100 ml) was added to the residue and the suspension stirred several minutes, the suspension was filtered and the filtrate was acidified with concentrated hydrochloric acid (red to litmus paper). The mixture was filtered and the residue was washed sequentially with 1×25 ml water, 1×10 ml 2-propanol and 1×10 ml ethyl ether. The suction-dried residue was recrystallized from methanol to give 3 g of the subject compound; m.p. 224°-227° C.

Anal. calc. for $C_9H_9N_3O_3S_2$: C,39.8; H,3.4; N,15.5; Found: C,39.4; H,3.4; N,15.4.

EXAMPLE 3

2-[5-(Methylthio)-1,3,4-oxadiazol-2-yl]benzenemethanesulfonamide

To a solution containing 0.62 g of potassium hydroxide in 50 ml of methanol was added 3 g of the oxadiazole prepared in Example 2. After stirring about five minutes, 2 g of methyl iodide was added. The suspension was refluxed 0.5 hour, cooled to 30° C., an extra 10 g of methyl iodide was added, and the suspension was refluxed an additional two hours, then concentrated in vacuo. After water was added to the residue, the suspension was filtered and the solid was washed with 1×50 ml of water. The suction-dried solid was recrystallized from 2-propanol to give 2 g of the subject compound; m.p. 138°-140° C.

Anal. calc. for $C_{10}H_{11}N_3O_3S_2$: C,42.1; H,3.9; N,14.7; Found; C,42.3; H,3.9; N,14.6;

EXAMPLE 4

N-[(4,6-Dimethoxypyrimidin-2-yl)aminocarbonyl]-2-[5-(methylthio)1,3,4-oxadiazol-2-yl]benzenemethanesulfonamide To a solution containing 0.62 g of the sulfonamide prepared in Example 3 contained in 10 ml of p-dioxane was added 0.6 g of phenyl(4.6-dimethoxy pyrimidin-2-yl)carbamate followed by dropwise addition of 0.33 g of 1,5-diazbicyclo[5.4.0]undec-5-ene (DBU). The solution was stirred at room temperature for two hours then diluted with about 100 ml of water. The clear solution was acidified with concentrated hydrochloric acid (red to litmus paper), to give a viscous oil. The oil was triturated by decanting off the aqueous solvent and stirring the oil residue in about 5 ml of acetonitrile. After filtering the suspension, the solid residue was washed with 1×5 ml of warm ethyl acetate to give 0.26 g of the subject compound; m.p. 174°-177° C.

Anal, calc. for $C_{17}H_{18}N_6O_6S_2$: C,43.8; H,3.9; N,18.0; Found: C,43.5; H,3.9; N,18.1.

NMR ($CDCl_3$, DMSO-$d_6$) ppm: δ2.8 (s, 3H, $SCH_3$); 3.75 (s, 6H, $OCH_3$); 5.5 (s, 2H, $CH_2$); 5.7 (s, 1H, pyrimidin); 7.4-8.1 (m, 4H; arom.); and 9.7 (s, 1H, NH).

IR (nujol): 1680 $cm^{-1}$ (C=O).

EXAMPLE 5

N-[(4-Methoxy-6-methyl1,3,5-triazin-2-yl)aminocarbonyl]-2-[5-methylthio)-1,3,4-oxadiazol-2-benzenemethanesulfonamide By the procedure of Example 4, 0.62 g of the sulfonamide of Example 3 was reacted with 0.57 g of phenyl (4-methoxy-6-methyl-1,3,5-triazin-2-yl)carbamate and 0.33 g of DBU in 10 ml of p-dioxane. After stirring two hours at room temperature the solution was diluted with about 75 ml of water and acidified with concentrated hydrochloric acid (red to litmus). Followed filtration, the residue was washed with 1×5 ml of warm ethyl acetate to give 0.28 g of the subject compound; m.p. 175°-177° C.

IR (nujol): 1730 $cm^{-1}$ (C=O).

NMR ($CDCl_{13}$) ppm: δ2.6 (s, 3H, $OCH_3$); 2.8 (s, 3H, $SCH_3$); 4.0 (s, 3H, $CH_3$); 5.6 (s, 2H, $CH_2$); and 7.5-8.0 (m, arom. and NH).

EXAMPLE 6

N-(Butylaminocarbonyl)-2[5-(methylthio)-1,3,4-oxadiazol-2-yl]benzenemethanesulfonamide A suspension containing 16 g of the sulfonamide of Example 3, 7.7 g of potassium carbonate and 6.7 g of n-butylisocyanate in 130 of 2-butanone was refluxed for 4 hours, then stirred overnight at room temperature. After concentrating the mixture in vacuo, the residue was diluted with about 150 ml of water and the solution was washed 1×100 ml of ethyl ether. The aqueous layer was acidified with concentrated hydrochloric acid (red to litmus paper) and the resulting suspension was filtered, the suction-dried overnight to give 20 g of the subject compound; m.p. 156°-159° C. IR (nujol): 1680 $cm^{-1}$ (C=O).

EXAMPLE 7

2-[5-(Methylthio)-1,3,4-oxadiazol2-yl]benzenemethanesulfonyl isocyanate

A suspension of 18.4 g of compound prepared in Example 6 in 180 ml of xylene containing 0.8 g DABCO was heated at 130°-135° C. while 3.9 ml of phosgene was added portionwise at a rate to maintain a reflux temperature of 130°-135° C. The mixture was refluxed for an additional 2 hours, cooled under nitrogen to room temperature, filtered, and the filtrate was concentrated to dryness in vacuo. A sample of the crude oily product displayed a characteristic sulfonyl isocyanate band in the IR at 2200 $cm^{-1}$.

EXAMPLE 8

N-[(4-Methyl-6-methoxypyrimidin-2-yl)aminocarbonyl]-2-[5-(methylthio)-1,3,4-oxadiazol-2-yl]benzenemethanesulfonamide To a suspension of 0.33 g of 2-amino-4-methyl-6-methoxypyrimidine in 10 ml of acetonitrile was added 1 g of crude sulfonyl isocyanate prepared in Example 7. The suspension was stirred at room temperature overnight, then filtered, the residue was washed with 25 ml of ethyl ether and suction dried to give 0.7 g of the subject compound; m.p. 194°-196° C.

NMR($CDCl_3$, DMSO): ppm δ2.3 (s, 3H, $CH_3$) 2.8 (s, 3H, $SCH_3$); 3.8 (s, 3H, $OCH_3$); 5.6 (s, 2H, $CH_2$); 6.3 (s, 1H, pyrimidin); 7.4-7.9 (m, 4H, arom.).

IR (nujol): 1710 $cm^{-1}$ (C=O).

Using the techniques described in Equations 1-12 and Examples 4, 5, and 8, or simple modification thereof, the following compounds in Tables I-V can be made by one skilled in the art.

TABLE I

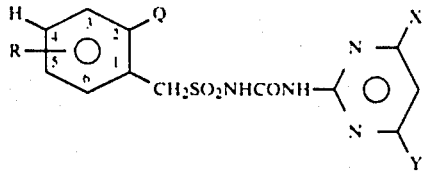

| Q | R | X | Y | m.p. °C. |
|---|---|---|---|---|
| Q-1 | H | $CH_3$ | $CH_3$ | |
| Q-1 | H | $OCH_3$ | $OCH_3$ | |
| Q-1 | H | $CH_3$ | $OCH_3$ | |
| Q-1 | H | Cl | $OCH_3$ | |
| Q-1 | H | Br | $OCH_3$ | |
| Q-2 | H | $CH_3$ | $CH_3$ | |
| Q-2 | H | $OCH_3$ | $OCH_3$ | |
| Q-2 | H | $CH_3$ | $OCH_3$ | |

TABLE I-continued

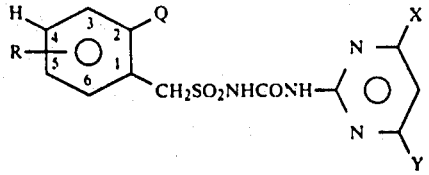

| Q | R | X | Y | m.p. °C. |
|---|---|---|---|---|
| Q-2 | H | Cl | $OCH_3$ | |
| Q-2 | H | Br | $OCH_3$ | |
| Q-3 | H | $CH_3$ | $CH_3$ | |
| Q-3 | H | $OCH_3$ | $OCH_3$ | |
| Q-3 | H | $CH_3$ | $OCH_3$ | |
| Q-3 | H | Cl | $OCH_3$ | |
| Q-4 | H | $CH_3$ | $CH_3$ | |
| Q-4 | H | $CH_3$ | $OCH_3$ | |
| Q-4 | H | $OCH_3$ | $OCH_3$ | |
| Q-4 | H | Cl | $OCH_3$ | |
| Q-5 | H | $CH_3$ | $CH_3$ | |
| Q-5 | H | $OCH_3$ | $OCH_3$ | |
| Q-5 | H | $CH_3$ | $OCH_3$ | |
| Q-5 | H | Cl | $OCH_3$ | |
| Q-6 | H | $CH_3$ | $CH_3$ | |
| Q-6 | H | $OCH_3$ | $OCH_3$ | |
| Q-6 | H | $CH_3$ | $OCH_3$ | |
| Q-6 | H | Cl | $OCH_3$ | |
| Q-7 ($R_1$ = $SCH_3$) | H | $OCH_3$ | $OCH_3$ | 174-177 |
| Q-7 ($R_1$ = $SCH_3$) | H | $CH_3$ | $OCH_3$ | 194-196 |
| Q-7 ($R_1$ = $SC_2H_5$) | H | $OCH_3$ | $OCH_3$ | 164-167 |
| Q-7 ($R_1$ = $SC_2H_5$) | H | $CH_3$ | $OCH_3$ | |
| Q-7 ($R_1$ = $SCH_2CH_2CH_3$) | H | $OCH_3$ | $OCH_3$ | |
| Q-7 ($R_1$ = $SCH_2CH_2CH_3$) | H | $CH_3$ | $OCH_3$ | |
| Q-7 ($R_1$ = $SCH(CH_3)_2$) | H | $OCH_3$ | $OCH_3$ | |
| Q-7 ($R_1$ = $SCH(CH_3)_2$) | H | $CH_3$ | $OCH_3$ | |
| Q-7 ($R_1$ = S-n-butyl) | H | $OCH_3$ | $OCH_3$ | |
| Q-7 ($R_1$ = S-n-butyl) | H | $CH_3$ | $OCH_3$ | |
| Q-7 ($R_1$ = $OCH_3$) | H | $OCH_3$ | $OCH_3$ | |
| Q-7 ($R_1$ = $OCH_3$) | H | $CH_3$ | $OCH_3$ | |
| Q-7 ($R_1$ = $OCH_3$) | H | $CH_3$ | $CH_3$ | |
| Q-7 ($R_1$ = $OCH_3$) | H | Cl | $OCH_3$ | |
| Q-7 ($R_1$ = $OC_2H_5$) | H | $CH_3$ | $OCH_3$ | |
| Q-7 ($R_1$ = $OC_2H_5$) | H | $OCH_3$ | $OCH_3$ | |
| Q-7 ($R_1$ = $OC_2H_5$) | H | $CH_3$ | $CH_3$ | |
| Q-7 ($R_1$ = $OC_2H_5$) | H | Cl | $OCH_3$ | |
| Q-7 ($R_1$ = H) | H | $OCH_3$ | $OCH_3$ | |
| Q-7 ($R_1$ = H) | H | $CH_3$ | $OCH_3$ | |
| Q-7 ($R_1$ = $SCH_2CN$) | H | $OCH_3$ | $OCH_3$ | |
| Q-7 ($R_1$ = $SCH_2CN$) | H | $CH_3$ | $OCH_3$ | |
| Q-7 ($R_1$ = $SCF_2H$) | H | $OCH_3$ | $OCH_3$ | |
| Q-7 ($R_1$ = $SCF_2H$) | H | $CH_3$ | $OCH_3$ | |
| Q-8 | H | $OCH_3$ | $OCH_3$ | |
| Q-8 | H | $CH_3$ | $OCH_3$ | |
| Q-8 | H | $CH_3$ | $CH_3$ | |
| Q-8 | H | Cl | $OCH_3$ | |
| Q-9 | H | $OCH_3$ | $OCH_3$ | |
| Q-9 | H | $CH_3$ | $OCH_3$ | |
| Q-9 | H | $CH_3$ | $CH_3$ | |
| Q-9 | H | Cl | $OCH_3$ | |
| Q-10 | H | $OCH_3$ | $OCH_3$ | |
| Q-10 | H | $CH_3$ | $OCH_3$ | |
| Q-10 | H | $CH_3$ | $CH_3$ | |
| Q-11 ($R_2$ = Cl) | H | $OCH_3$ | $OCH_3$ | |
| Q-11 ($R_2$ = Cl) | H | $CH_3$ | $OCH_3$ | |
| Q-11 ($R_2$ = Cl) | H | Cl | $OCH_3$ | |
| Q-11 ($R_2$ = Cl) | H | $CH_3$ | $CH_3$ | |
| Q-11 ($R_2$ = H) | H | $OCH_3$ | $OCH_3$ | |
| Q-11 ($R_2$ = H) | H | $CH_3$ | $OCH_3$ | |
| Q-12 | H | $OCH_3$ | $OCH_3$ | |
| Q-12 | H | $CH_3$ | $OCH_3$ | |
| Q-13 | H | $OCH_3$ | $OCH_3$ | |
| Q-13 | H | $CH_3$ | $OCH_3$ | |
| Q-13 | H | $CH_3$ | $CH_3$ | |
| Q-13 | H | Cl | $OCH_3$ | |
| Q-14 | H | $OCH_3$ | $OCH_3$ | |
| Q-14 | H | $CH_3$ | $OCH_3$ | |
| Q-14 | H | $CH_3$ | $CH_3$ | |
| Q-14 | H | Cl | $OCH_3$ | |
| Q-15 | H | $CH_3$ | $CH_3$ | |
| Q-15 | H | $OCH_3$ | $OCH_3$ | |

TABLE I-continued

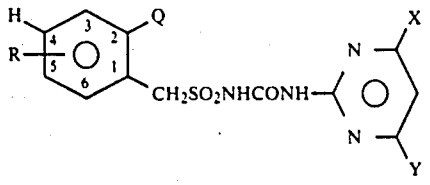

| Q | R | X | Y | m.p. °C. |
|---|---|---|---|---|
| Q-15 | H | $CH_3$ | $OCH_3$ | |
| Q-15 | H | Cl | $OCH_3$ | |
| Q-16 | H | $CH_3$ | $CH_3$ | |
| Q-16 | H | $OCH_3$ | $CH_3$ | |
| Q-16 | H | $OCH_3$ | $OCH_3$ | |
| Q-16 | H | $CH_3$ | $CH_3$ | |
| Q-16 | H | Cl | $OCH_3$ | |
| Q-17 | H | $OCH_3$ | $OCH_3$ | |
| Q-17 | H | $CH_3$ | $OCH_3$ | |
| Q-18 | H | $OCH_3$ | $OCH_3$ | |
| Q-18 | H | $CH_3$ | $OCH_3$ | |
| Q-18 | H | $CH_3$ | $CH_3$ | |
| Q-18 | H | Cl | $OCH_3$ | |
| Q-19 | H | $OCH_3$ | $OCH_3$ | |
| Q-19 | H | $CH_3$ | $OCH_3$ | |
| Q-20 | H | $OCH_3$ | $OCH_3$ | |
| Q-20 | H | $CH_3$ | $OCH_3$ | |
| Q-21 | H | $CH_3$ | $CH_3$ | |
| Q-21 | H | $OCH_3$ | $CH_3$ | |
| Q-21 | H | $OCH_3$ | $OCH_3$ | |
| Q-21 | H | Cl | $OCH_3$ | |
| Q-22 | H | $OCH_3$ | $OCH_3$ | |
| Q-22 | H | $CH_3$ | $OCH_3$ | |
| Q-23 | H | $OCH_3$ | $OCH_3$ | |
| Q-23 | H | $CH_3$ | $OCH_3$ | |
| Q-23 | H | $CH_3$ | $CH_3$ | |
| Q-23 | H | Cl | $OCH_3$ | |
| Q-24 | H | $OCH_3$ | $OCH_3$ | |
| Q-24 | H | $CH_3$ | $OCH_3$ | |
| Q-25 | H | $OCH_3$ | $OCH_3$ | |
| Q-25 | H | $CH_3$ | $OCH_3$ | |
| Q-26 | H | $CH_3$ | $OCH_3$ | |
| Q-26 | H | $OCH_3$ | $OCH_3$ | |
| Q-27 | H | $OCH_3$ | $CH_3$ | |
| Q-27 | H | $OCH_3$ | $OCH_3$ | |
| Q-1 | H | $OC_2H_5$ | $CH_3$ | |
| Q-1 | H | F | $OCH_3$ | |
| Q-2 | H | I | $OCH_3$ | |
| Q-8 | H | $OCF_2H$ | $OCH_3$ | |
| Q-9 | H | $CH_2F$ | $CH_3$ | |
| Q-16 | H | $OCH_2CH_2F$ | $CH_3$ | |
| Q-7 ($R_1$ = $CH_3$) | H | $OCH_2CHF_2$ | $CH_3$ | |
| Q-1 | H | $OCH_2CF_3$ | $OCH_3$ | |
| Q-1 | H | $CF_3$ | $OCH_3$ | |
| Q-1 | H | F | $OCH_3$ | |
| Q-1 | H | $OCH_3$ | H | |
| Q-1 | H | Cl | $OC_2H_5$ | |
| Q-1 | H | $OCH_3$ | $CH_2OCH_3$ | |
| Q-2 | H | Cl | $NHCH_3$ | |
| Q-3 | H | $OC_2H_5$ | $N(OCH_3)CH_3$ | |
| Q-16 | H | $CH_3$ | $N(CH_3)_2$ | |
| Q-1 | H | $OCH_3$ | $C_2H_5$ | |
| Q-8 | H | $CF_3$ | $CF_3$ | |
| Q-9 | H | $CH_3$ | $SCH_3$ | |
| Q-10 | H | $OCH_3$ | $OCH_2CH{=}CH_2$ | |
| Q-11 ($R_2$ = Cl) | H | $CH_3$ | $OCH_2C{\equiv}CH$ | |
| Q-15 | H | $OCH_3$ | $CH_2OCH_2CH_3$ | |
| Q-1 | H | $CH_3$ | $OCH_2CH_2OCH_3$ | |
| Q-2 | H | $CH_3$ | $CH_2SCH_3$ | |
| Q-1 | H | $CH_3$ | CHO | |
| Q-18 | H | $CH_3$ | O ‖ $CCH_3$ | |
| Q-1 | H | $OCH_3$ | $CH(OCH_3)_2$ | |
| Q-8 | H | $OCH_3$ | $CH(OC_2H_5)_2$ | |
| Q-9 | H | $OCH_3$ | $CH(SCH_3)_2$ | |
| Q-10 | H | $OCH_3$ | $C(CH_3)(OCH_3)_2$ | |

TABLE I-continued

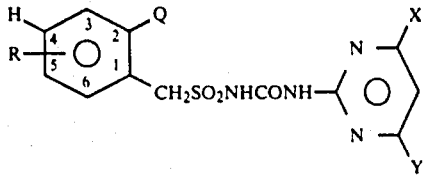

| Q | R | X | Y | m.p. °C. |
|---|---|---|---|---|
| Q-1 | H | $OCH_3$ | 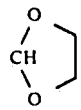 | |
| Q-16 | H | $CH_3$ | 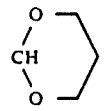 | |
| Q-21 | H | $OCH_3$ | 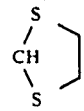 | |
| Q-24 | H | $OCH_3$ | 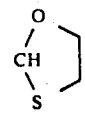 | |
| Q-23 | H | $OCH_3$ | 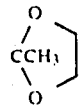 | |
| Q-1 | H | $OCH_3$ | 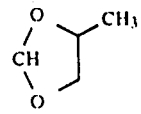 | |
| Q-12 | H | $OCH_3$ | 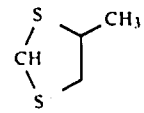 | |
| Q-17 | H | $OCH_3$ | 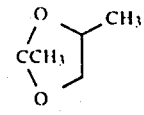 | |
| Q-18 | H | Cl | $OCF_2H$ | |
| Q-21 | H | $CH_3$ | $SCF_2H$ | |
| Q-1 | H | $OCH_3$ | 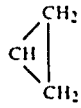 | |
| Q-8 | 3-F | $OCH_3$ | $OCH_3$ | |
| Q-9 | 6-Cl | $OCH_3$ | $CH_3$ | |
| Q-1 | 5-Br | $OCH_3$ | $OCH_3$ | |
| Q-7 ($R_1$ = $SC_2H_5$) | 5-$CH_3$ | $OCH_3$ | $OCH_3$ | |
| Q-7 ($R_1$ = $SCH_3$) | 5-$CF_3$ | $OCH_3$ | $OCH_3$ | |
| Q-7 ($R_1$ = $SCH_3$) | 5-$OCH_3$ | $OCH_3$ | $OCH_3$ | |
| Q-7 ($R_1$ = $SCH_3$) | 6-$OCF_2H$ | $OCH_3$ | $OCH_3$ | |
| Q-7 ($R_1$ = $SCH_3$) | 6-$SCF_2H$ | $OCH_3$ | $OCH_3$ | |
| Q-7 ($R_1$ = $SCH_2CH{=}CH_2$) | H | $OCH_3$ | $OCH_3$ | 165-168 |
| Q-7 ($R_1$ = $SCH_2CH{=}CH_2$) | H | $CH_3$ | $OCH_3$ | |
| Q-1 | H | $CH_3$ | $CH_2OCH_3$ | |
| Q-1 | H | $OCH_3$ | $OCF_2H$ | |

TABLE I-continued

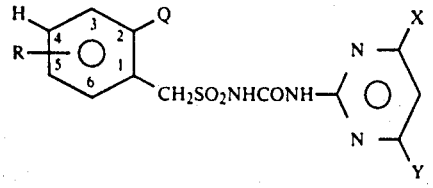

| Q | R | X | Y | m.p. °C. |
|---|---|---|---|---|
| Q-28 | H | $CH_3$ | $CH_3$ | |
| Q-28 | H | $OCH_3$ | $CH_3$ | |
| Q-28 | H | $OCH_3$ | $OCH_3$ | |
| Q-28 | H | Cl | $OCH_3$ | |
| Q-29 | H | $CH_3$ | $CH_3$ | |
| Q-29 | H | $OCH_3$ | $CH_3$ | |
| Q-29 | H | $OCH_3$ | $OCH_3$ | |
| Q-29 | H | Cl | $OCH_3$ | |
| Q-30 | H | $CH_3$ | $CH_3$ | |
| Q-30 | H | $OCH_3$ | $CH_3$ | |
| Q-30 | H | $OCH_3$ | $OCH_3$ | |
| Q-30 | H | Cl | $OCH_3$ | |
| Q-31 | H | $CH_3$ | $CH_3$ | |
| Q-31 | H | $OCH_3$ | $CH_3$ | |
| Q-31 | H | $OCH_3$ | $OCH_3$ | |
| Q-31 | H | Cl | $OCH_3$ | |
| Q-32 | H | $CH_3$ | $CH_3$ | |
| Q-32 | H | $OCH_3$ | $CH_3$ | |
| Q-32 | H | $OCH_3$ | $OCH_3$ | |
| Q-32 | H | Cl | $OCH_3$ | |
| Q-33 | H | $CH_3$ | $CH_3$ | |
| Q-33 | H | $OCH_3$ | $CH_3$ | |
| Q-33 | H | $OCH_3$ | $OCH_3$ | |
| Q-33 | H | Cl | $OCH_3$ | |
| Q-7 ($R_1$ = $SCH_3$) | 5-$SCH_3$ | $OCH_3$ | $OCH_3$ | |
| Q-1 | 5-$SCH_3$ | $OCH_3$ | $OCH_3$ | |
| Q-7 ($R_1$ = $C_2H_5$) | H | $OCH_3$ | $OCH_3$ | |
| Q-7 ($R_1$ = $CH_3$) | H | $OCH_3$ | $OCH_3$ | |
| Q-7 ($R_1$ = SH) | H | $OCH_3$ | $OCH_3$ | |
| Q-7 ($R_1$ = SH) | H | $CH_3$ | $OCH_3$ | |

TABLE II

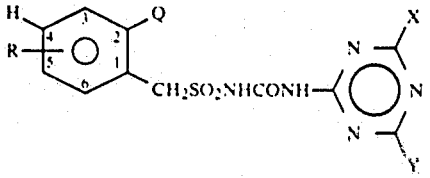

| Q | R | X | Y | m.p. °C. |
|---|---|---|---|---|
| Q-1 | H | $CH_3$ | $OCH_3$ | |
| Q-1 | H | $OCH_3$ | $OCH_3$ | |
| Q-2 | H | $CH_3$ | $OCH_3$ | |
| Q-2 | H | $OCH_3$ | $OCH_3$ | |
| Q-3 | H | $OCH_3$ | $OCH_3$ | |
| Q-3 | H | $CH_3$ | $OCH_3$ | |
| Q-4 | H | $CH_3$ | $OCH_3$ | |
| Q-5 | H | $CH_3$ | $OCH_3$ | |
| Q-6 | H | $CH_3$ | $OCH_3$ | |
| Q-7 ($R_1$ = $SCH_3$) | H | $CH_3$ | $OCH_3$ | 175-177 |
| Q-7 ($R_1$ = $SCH_3$) | H | $OCH_3$ | $OCH_3$ | 180-185 |
| Q-7 ($R_1$ = $SC_2H_5$) | H | $OCH_3$ | $CH_3$ | |
| Q-7 ($R_1$ = $SC_2H_5$) | H | $OCH_3$ | $OCH_3$ | |
| Q-7 ($R_1$ = $SCH_2CH_2CH_3$) | H | $OCH_3$ | $CH_3$ | |
| Q-7 ($R_1$ = $SCH_2CH_2CH_3$) | H | $OCH_3$ | $OCH_3$ | |
| Q-7 ($R_1$ = $SCH(CH_3)_2$) | H | $OCH_3$ | $CH_3$ | |
| Q-7 ($R_1$ = $SCH(CH_3)_2$) | H | $OCH_3$ | $OCH_3$ | |
| Q-7 ($R_1$ = S-n-butyl) | H | $CH_3$ | $OCH_3$ | |
| Q-7 ($R_1$ = $SCH_2CN$) | H | $OCH_3$ | $CH_3$ | |
| Q-7 ($R_1$ = $SCH_2CN$) | H | $OCH_3$ | $OCH_3$ | |
| Q-7 ($R_1$ = $SCF_2H$) | H | $CH_3$ | $OCH_3$ | |
| Q-7 ($R_1$ = $SCF_2H$) | H | $OCH_3$ | $OCH_3$ | |
| Q-7 ($R_1$ = $OCH_3$) | H | $CH_3$ | $OCH_3$ | |
| Q-7 ($R_1$ = $OCH_3$) | H | $OCH_3$ | $OCH_3$ | |
| Q-7 ($R_1$ = $OC_2H_5$) | H | $OCH_3$ | $CH_3$ | |
| Q-7 ($R_1$ = H) | H | $CH_3$ | $OCH_3$ | |

TABLE II-continued

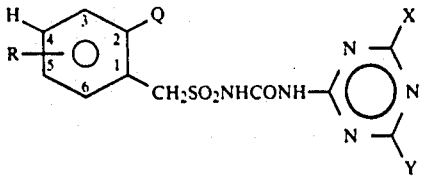

| Q | R | X | Y | m.p. °C. |
|---|---|---|---|---|
| Q-7 ($R_1$ = H) | H | $OCH_3$ | $OCH_3$ | |
| Q-8 | H | $CH_3$ | $OCH_3$ | |
| Q-8 | H | $OCH_3$ | $OCH_3$ | |
| Q-9 | H | $OCH_3$ | $CH_3$ | |
| Q-9 | H | $OCH_3$ | $OCH_3$ | |
| Q-10 | H | $CH_3$ | $OCH_3$ | |
| Q-11 ($R_2$ = Cl) | H | $CH_3$ | $OCH_3$ | |
| Q-11 ($R_2$ = H) | H | $CH_3$ | $OCH_3$ | |
| Q-12 | H | $CH_3$ | $OCH_3$ | |
| Q-13 | H | $CH_3$ | $OCH_3$ | |
| Q-13 | H | $OCH_3$ | $OCH_3$ | |
| Q-14 | H | $CH_3$ | $OCH_3$ | |
| Q-15 | H | $CH_3$ | $OCH_3$ | |
| Q-16 | H | $OCH_3$ | $OCH_3$ | |
| Q-16 | H | $CH_3$ | $OCH_3$ | |
| Q-17 | H | $CH_3$ | $OCH_3$ | |
| Q-18 | H | $CH_3$ | $OCH_3$ | |
| Q-19 | H | $CH_3$ | $OCH_3$ | |
| Q-20 | H | $CH_3$ | $OCH_3$ | |
| Q-21 | H | $CH_3$ | $OCH_3$ | |
| Q-22 | H | $CH_3$ | $OCH_3$ | |
| Q-23 | H | $CH_3$ | $OCH_3$ | |
| Q-23 | H | $OCH_3$ | $OCH_3$ | |
| Q-24 | H | $CH_3$ | $OCH_3$ | |
| Q-25 | H | $CH_3$ | $OCH_3$ | |
| Q-26 | H | $CH_3$ | $OCH_3$ | |
| Q-27 | H | $CH_3$ | $OCH_3$ | |
| Q-8 | 3-F | $OCH_3$ | $CH_3$ | |
| Q-9 | 6-Cl | $OCH_3$ | $CH_3$ | |
| Q-1 | 5-Br | $CH_3$ | $OCH_3$ | |
| Q-7 ($R_1$ = $SC_2H_5$) | 5-$CH_3$ | $OCH_3$ | $OCH_3$ | |
| Q-7 ($R_1$ = $SCH_3$) | 5-$CF_3$ | $CH_3$ | $OCH_3$ | |
| Q-7 ($R_1$ = $SCH_3$) | 5-$OCH_3$ | $CH_3$ | $OCH_3$ | |
| Q-7 ($R_1$ = $SCH_3$) | 6-$OCF_2H$ | $CH_3$ | $OCH_3$ | |
| Q-7 ($R_1$ = $SCH_3$) | 6-$SCF_2H$ | $OCH_3$ | $OCH_3$ | |
| Q-1 | H | $CH_3$ | $OC_2H_5$ | |
| Q-1 | H | $OC_2H_5$ | $NHCH_3$ | |
| Q-8 | H | $OCH_3$ | $N(OCH_3)CH_3$ | |
| Q-9 | H | $CH_3$ | $N(OCH_3)CH_3$ | |
| Q-1 | I | $OCF_2H$ | $N(OCH_3)CH_3$ | |
| Q-4 | H | $OCH_3$ | $N(CH_3)_2$ | |
| Q-1 | H | $OCH_3$ | $C_2H_5$ | |
| Q-16 | H | $OCH_3$ | $SCH_3$ | |
| Q-17 | H | $OCH_3$ | $OCH_2CH{=}CH_2$ | |
| Q-1 | H | $CH_3$ | $CH(OCH_3)_2$ | |
| Q-1 | H | $OCH_3$ | $OCF_2H$ | |
| Q-1 | H | $OCH_3$ | $OCH_2CF_3$ | |
| Q-8 | H | $CH_3$ | $OCH_2CF_3$ | |
| Q-16 | H | $OCH_3$ | $CH(CH_3)(OCH_3)_2$ | |
| Q-2 | H | $CH_3$ | 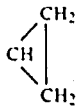 | |
| Q-1 | H | $OCH_3$ | 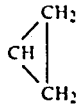 | |
| Q-7 ($R_1$ = $SCH_2CH{=}CH_2$) | H | $OCH_3$ | $OCH_3$ | |
| Q-7 ($R_1$ = $SCH_2CH{=}CH_2$) | H | $CH_3$ | $OCH_3$ | |
| Q-28 | H | $CH_3$ | $CH_3$ | |
| Q-28 | H | $OCH_3$ | $CH_3$ | |
| Q-29 | H | $CH_3$ | $CH_3$ | |
| Q-29 | H | $OCH_3$ | $CH_3$ | |
| Q-30 | H | $CH_3$ | $CH_3$ | |
| Q-30 | H | $OCH_3$ | $CH_3$ | |
| Q-31 | H | $CH_3$ | $CH_3$ | |

TABLE II-continued

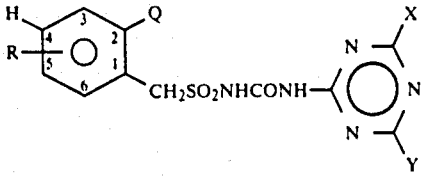

| Q | R | X | Y | m.p. °C. |
|---|---|---|---|---|
| Q-31 | H | $OCH_3$ | $CH_3$ | |
| Q-32 | H | $CH_3$ | $CH_3$ | |
| Q-32 | H | $OCH_3$ | $CH_3$ | |
| Q-33 | H | $CH_3$ | $CH_3$ | |
| Q-33 | H | $OCH_3$ | $CH_3$ | |
| Q-7 ($R_1$ = SH) | H | $OCH_3$ | $CH_3$ | |
| Q-7 ($R_1$ = SH) | H | $OCH_3$ | $OCH_3$ | |

TABLE III

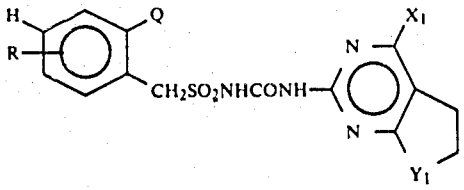

| Q | R | $X_1$ | $Y_1$ | m.p. °C. |
|---|---|---|---|---|
| Q-1 | H | $CH_3$ | O | |
| Q-1 | H | $OCH_3$ | O | |
| Q-2 | H | $CH_3$ | O | |
| Q-2 | H | $OCH_3$ | O | |
| Q-3 | H | $CH_3$ | O | |
| Q-7 ($R_1$ = $SCH_3$) | H | $CH_3$ | O | 184-187 |
| Q-7 ($R_1$ = $SCH_3$) | H | $OCH_3$ | O | |
| Q-7 ($R_1$ = $SCH_3$) | H | $OC_2H_5$ | O | |
| Q-7 ($R_1$ = $SCH_3$) | H | $OCF_2H$ | O | |
| Q-7 ($R_1$ = $SCH_3$) | H | $OCH_3$ | $CH_2$ | |
| Q-7 ($R_1$ = $SCH_3$) | H | $CH_3$ | $CH_2$ | |
| Q-8 | H | $CH_3$ | O | |
| Q-9 | H | $CH_3$ | O | |
| Q-16 | H | $CH_3$ | O | |
| Q-21 | H | $CH_3$ | O | |
| Q-23 | H | $CH_3$ | O | |

TABLE IV

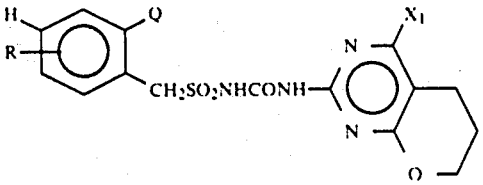

| Q | R | $X_1$ | m.p. °C. |
|---|---|---|---|
| Q-1 | H | $CH_3$ | |
| Q-2 | H | $CH_3$ | |
| Q-3 | H | $CH_3$ | |
| Q-7 ($R_1$ = $SCH_3$) | H | $CH_3$ | |
| Q-7 ($R_1$ = $SCH_3$) | H | $OCH_3$ | |
| Q-7 ($R_1$ = $SCH_3$) | H | $OC_2H_5$ | |
| Q-7 ($R_1$ = $SCH_3$) | H | $OCF_2H$ | |
| Q-8 | H | $CH_3$ | |
| Q-9 | H | $CH_3$ | |
| Q-16 | H | $CH_3$ | |
| Q-21 | H | $CH_3$ | |
| Q-23 | H | $CH_3$ | |

TABLE V

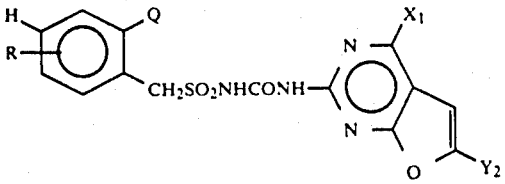

| Q | R | $X_1$ | $Y_2$ | m.p. °C. |
|---|---|---|---|---|
| Q-1 | H | $CH_3$ | $CH_3$ | |
| Q-2 | H | $CH_3$ | $CH_3$ | |
| Q-3 | H | $CH_3$ | $CH_3$ | |
| Q-7 ($R_1$ = $SCH_3$) | H | $CH_3$ | $CH_3$ | |
| Q-7 ($R_1$ = $SCH_3$) | H | $OCH_3$ | $CH_3$ | |
| Q-7 ($R_1$ = $SCH_3$) | H | $OC_2H_5$ | $CH_3$ | |
| Q-7 ($R_1$ = $SCH_3$) | H | $OCF_2H$ | $CH_3$ | |
| Q-7 ($R_1$ = $SCH_3$) | H | $CH_3$ | H | |
| Q-8 | H | $CH_3$ | $CH_3$ | |
| Q-9 | H | $CH_3$ | $CH_3$ | |
| Q-16 | H | $CH_3$ | $CH_3$ | |
| Q-21 | H | $CH_3$ | $CH_3$ | |
| Q-23 | H | $CH_3$ | $CH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE VI

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |

TABLE VI-continued

| | Active Ingredient | Weight Percent* Diluent(s) | Surfactant(s) |
|---|---|---|---|
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents" Chemical Publishing Co., Inc., New York, 1964, list surfactants and recommended uses. All formulations can contain minor amounts of additives to residue foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 9

Wettable Powder

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, re-blended, and packaged.

EXAMPLE 10

Wettable Powder

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

Granule

| | |
|---|---|
| Wettable Powder of Example 11 | 5% |
| attapulgite granules (U.S.S. 20-40 mesh; 0.84-0.42 mm) | 95% |

A slurry of wettable powder containing 25% solids is sprayed on the surface of attapulgite granules while tumbling in a double-cone blender. The granules are dried and packaged.

EXAMPLE 12

Extruded Pellet

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held on a U.S. Ser. No. 40 sieve (0.42 mm openings) may be packaged for use and the fines recycled.

EXAMPLE 13

Oil Suspension

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

Wettable Powder

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is re-blended and sifted through a U.S. Ser. No. 50 sieve (0.3 mm opening) and packaged.

EXAMPLE 15

Low Strength Granule

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

Aqueous Suspension

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

Solution

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide, sodium salt | 5% |
| water | 95% |

The salt is added directly to the water with stirring to produce the solution, which may then be packaged for use.

EXAMPLE 18

Low Strength Granule

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 19

Granule

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 20

High Strength Concentrate

| | |
|---|---|
| N-[(4,6-Dimethoxypyrimidin-2-yl)aminocarbonyl]-2-[5-(methylthio)-1,3,4-oxadiazol-2-yl]benzene-methanesulfonamide | 99% |
| silica aerogel | 0.5% |
| synthetic amorphous silica | 0.5% |

The ingredients are blended and ground in a hammer-mill to produce a material essentially all passing a U.S. Ser. No. 50 screen (0.3 mm opening). The concentrate may be formulated further if necessary.

EXAMPLE 21

Wettable Powder

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 22

Wettable Powder

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 23

Oil Suspension

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 24

Dust

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 25

Emulsifiable Concentrate

| | |
|---|---|
| N-[(4,6-Dimethoxypyrimidin-2-yl)aminocarbonyl]-2-[5-(methylthio)-1,3,4-oxadiazol-2-yl]benzenemethanesulfonamide | 20% |
| chlorobenzene | 74% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulants. Many of them have utility for broad-spectrum pre- and/or postemergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful to modify plant growth.

The rates of application for the compounds of the invention are determined by a number of factors, including their use as plant growth modifiers or as herbicides, the crop species involved, the types of weeds to be controlled, weather, and climate, formulations selected, mode of application, amount of foilage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commerical herbicide: examples of which are those of the triazine, triazole, uracil, urea, amide, diphenylether, carbamate and bipyridylium types. The compounds may also be used in combination with merfluidide.

The herbicidal properties of the subject compounds were dissolved in a number of greenhouse tests. The test procedures and results follow.

Test A

Seeds of crabgrass (Digitaria sp.), barnyardgrass (*Echinochloa crusqualli*), wild oats (*Avena fatua*), sicklepod (*Cassia obtusifolia*), morningglory (Ipomoea spp.), cocklebur (*Xanthium pensylvanicum*), velvetleaf (*Abutilon theophrasti*), cheatgrass (*Bromus secalinus*), sorghum, corn, soybean, cotton, sugar beet, rice, wheat and purple nutsedge (*Cyperus rotundus*) tubers were planted and treated preemergence with the test chemicals dissolved in a non-phytotoxic solvent. At the same time, these crop and weed species were treated with a soil/foilage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying the descriptive symbols have the following meanings:

C=chlorosis/necrosis;
B=burn;
D=defoliation;
E=emergence inhibition;
G=growth retardation;
H=formative effects;

BEST AVAILABLE COPY

U = unusual pigmentation;
X = axillary stimulation;
S = albinism; and
6Y = abscised buds or flowers.

Compounds

Compound 1

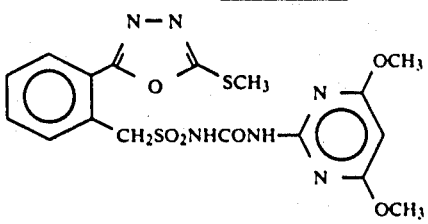

Compound 2

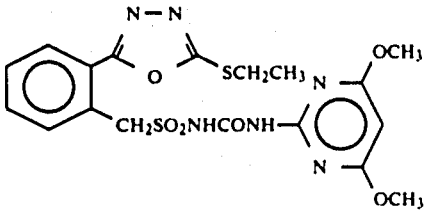

-continued

Compounds

Compound 3

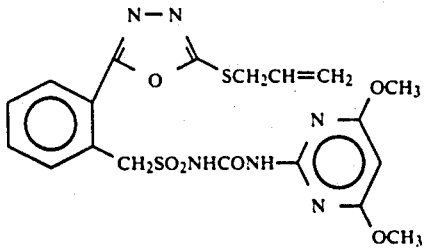

Compound 4

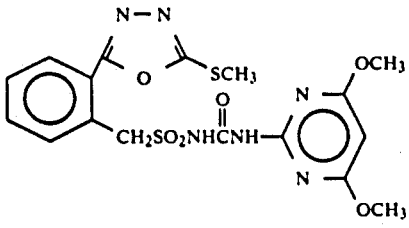

Compound 5

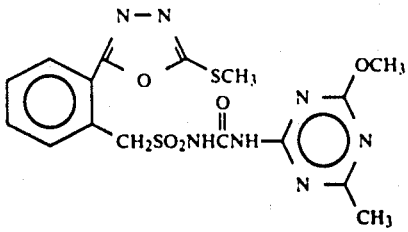

Compound 6

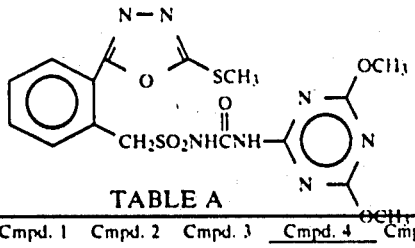

TABLE A

| | Cmpd. 1 | Cmpd. 2 | Cmpd. 3 | Cmpd. 4 | | Cmpd. 5 | Cmpd. 6 |
|---|---|---|---|---|---|---|---|
| Rate kg/ha | .05 | .05 | .05 | .4 | .05 | .4 | .4 |
| POST-EMERGENCE | | | | | | | |
| Morningglory | 5C,9G | 2C,6H | 4C,9G | 3C,7H | 2H | 3C,9H | 3C,9G |
| Cocklebur | 5G | 1C | 2C | 2C,2H | 0 | 3C,9G | 2G |
| Sicklepod | 2C | 2C | 4C,4H | | | | |
| Velvetleaf | | | | 3C,8H | 5G | 2C,5G | 3C,7G |
| Nutsedge | 2C,8G | 2C,7G | 8G | 0 | 0 | 3G | 0 |
| Crabgrass | 0 | 0 | 4G | 0 | 0 | 0 | 0 |
| Barnyardgrass | 3G | 0 | 4H | 0 | 0 | 0 | 0 |
| Cheatgrass | — | — | — | 0 | 0 | 2C | 2C,4G |
| Wild Oats | 0 | 0 | 0 | 0 | 0 | 0 | 4C,6G |
| Wheat | 0 | 0 | 0 | 0 | 0 | 2C,7G | 3C,7H |
| Corn | 0 | 0 | 2C,5H | 0 | 0 | 2C,7G | 3C,7H |
| Soybean | 2H,3G | 2C,5H | 3C,8H | 0 | 0 | 1H | 3C,6H |
| Rice | 3G | 0 | 3G | 0 | 0 | 3G | 4G |
| Sorghum | 3G | 0 | 2C,5G | 0 | 0 | 3C,7H | 3C,8H |
| Sugar beet | 3G | 2C | 9C | 3C,6H | 0 | 3C,8H | 3C,8H |
| Cotton | 5C,9G | 2C,5G | 4C,9G | 1C | 0 | 3C,9H | 3C,7G |
| PRE-EMERGENCE | | | | | | | |
| Morningglory | 9G | 2H | 9G | 2C | 0 | 2C,8G | 8G |
| Cocklebur | 3G | 0 | — | 2C | 2G | 1C | 0 |
| Sicklepod | 0 | 0 | 2C | | | | |
| Velvetleaf | | | | 2C,5G | 0 | 2G | 0 |
| Nutsedge | 0 | 0 | 7G | 0 | 0 | 0 | 0 |
| Barnyardgrass | 0 | 0 | 2C | 1C | 0 | 0 | 0 |
| Cheatgrass | — | — | — | 2G | 0 | 5G | 3G |
| Wild Oats | 0 | 0 | 0 | 0 | 0 | 1C | 2G |
| Wheat | 0 | 0 | 0 | 0 | 0 | 4G | 5G |
| Corn | 2C,3G | 0 | 2G | 1C | 0 | 2C,4G | 2G |
| Soybean | 2H | 0 | 2C,2H | 1C | 0 | 0 | 0 |
| Rice | 2C | 0 | 3C,5G | 1C | 0 | 2C,3G | 0 |
| Sorghum | 2C,6H | 0 | 2C,6H | 2C | 0 | 3C,8G | 2C,8G |
| Sugar beet | 3C,7G | 2H | 3C,5G | 5G | 0 | 3C,8H | 2G |
| Cotton | 3C,6G | 0 | 5G | 0 | 0 | 0 | 0 |

What is claimed is:

1. The compound methyl 2-[(aminosulfonyl)methyl]-benzoate.

* * * * *